United States Patent [19]

Ibrahim et al.

[11] Patent Number: 4,597,389
[45] Date of Patent: Jul. 1, 1986

[54] DEVICE FOR REMOVING OBJECTS FROM TUBULAR BODY PASSAGES

[76] Inventors: Adel A. Ibrahim, 50 Camelot Dr., Huntington, W. Va. 25701; Kevin D. Linville, 6257 Sturm Rd., Huntington, W. Va. 25705; Jerry E. Mays, 212 Short St., Huntington, W. Va. 25702

[21] Appl. No.: 705,410

[22] Filed: Feb. 25, 1985

Related U.S. Application Data

[63] Continuation of Ser. No. 430,016, Sep. 30, 1982, abandoned.

[51] Int. Cl.$^4$ ............................................. A61B 17/50
[52] U.S. Cl. ................................. 128/328; 128/303 R; 128/346; 128/356
[58] Field of Search ............... 128/DIG. 25, 346, 328, 128/356, 327, 303 R; 294/19 R, 63 A, 99, 90; 604/96

[56] References Cited

U.S. PATENT DOCUMENTS

| | | | |
|---|---|---|---|
| 2,944,552 | 7/1960 | Cannon | 128/304 |
| 3,538,917 | 11/1970 | Selker | 128/DIG. 25 X |
| 3,635,223 | 1/1972 | Klieman | 128/356 X |
| 3,750,194 | 8/1973 | Summers | 128/DIG. 25 X |
| 3,831,995 | 8/1974 | Duncan | 294/90 |
| 4,256,094 | 3/1981 | Kapp et al. | 128/DIG. 25 X |

FOREIGN PATENT DOCUMENTS

| | | | |
|---|---|---|---|
| 2847633 | 5/1979 | Fed. Rep. of Germany | 128/328 |
| 2845094 | 5/1980 | Fed. Rep. of Germany | 294/98.1 |
| 2427973 | 2/1980 | France | 294/119.3 |

Primary Examiner—Michael H. Thaler
Attorney, Agent, or Firm—Larson & Taylor

[57] ABSTRACT

A device and a method for removing objects from tubular body passages such as arteries, urinary passages, respiratory passages, alimentary canal passages, or other body passages. An elongated element has a ring at its distal end which surrounds the object. On the inside of the ring is a balloon which is constrained by the ring to inflate only inwardly, such that upon the inward inflation it engages and grasps the object to be removed. The device is then withdrawn, whereby the ring and the inflated balloon carry the object with it out of the body passage. Fluid such as air is introduced into and removed from the balloon via a line which runs from the balloon back along the elongated element to the proximal end of the device. A dye line may also be provided, running from the distal end of the device to the proximal end for introducing a dye into the body passage ahead of the ring for diagnostic purposes.

4 Claims, 8 Drawing Figures

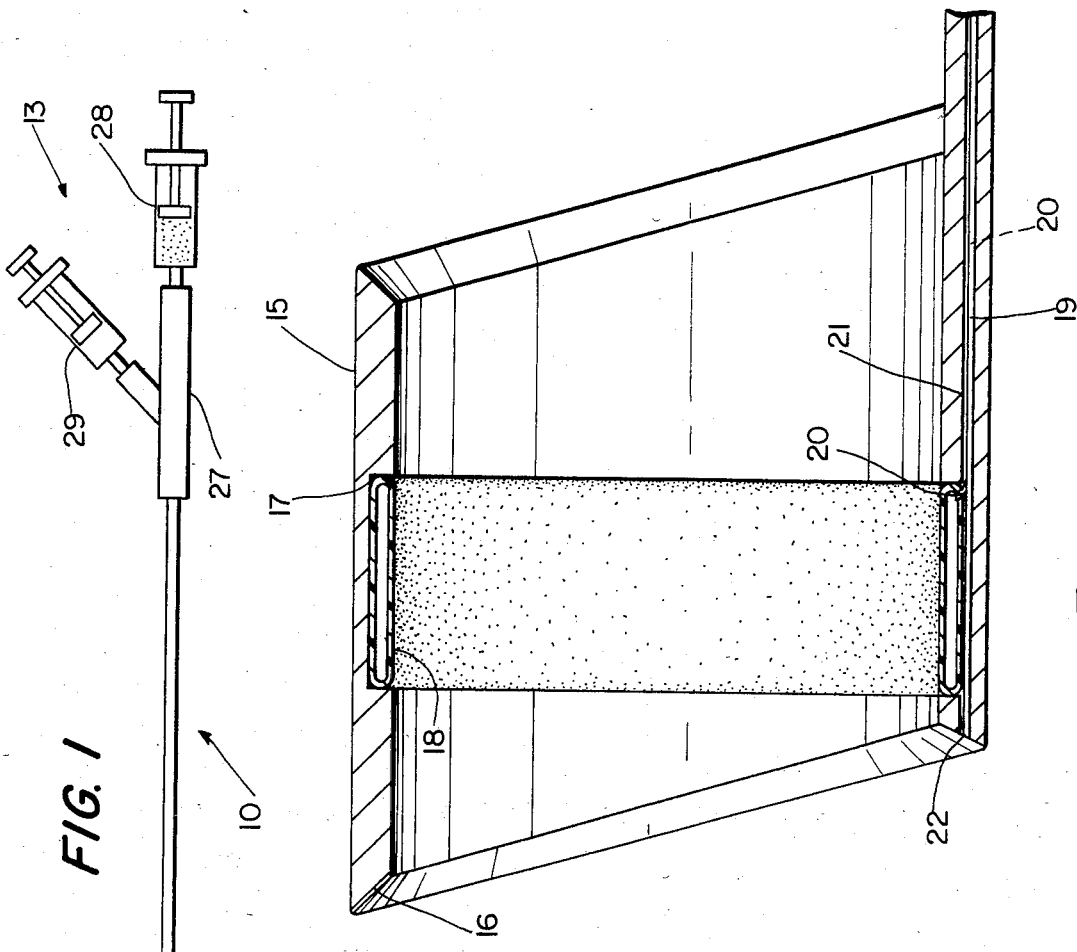
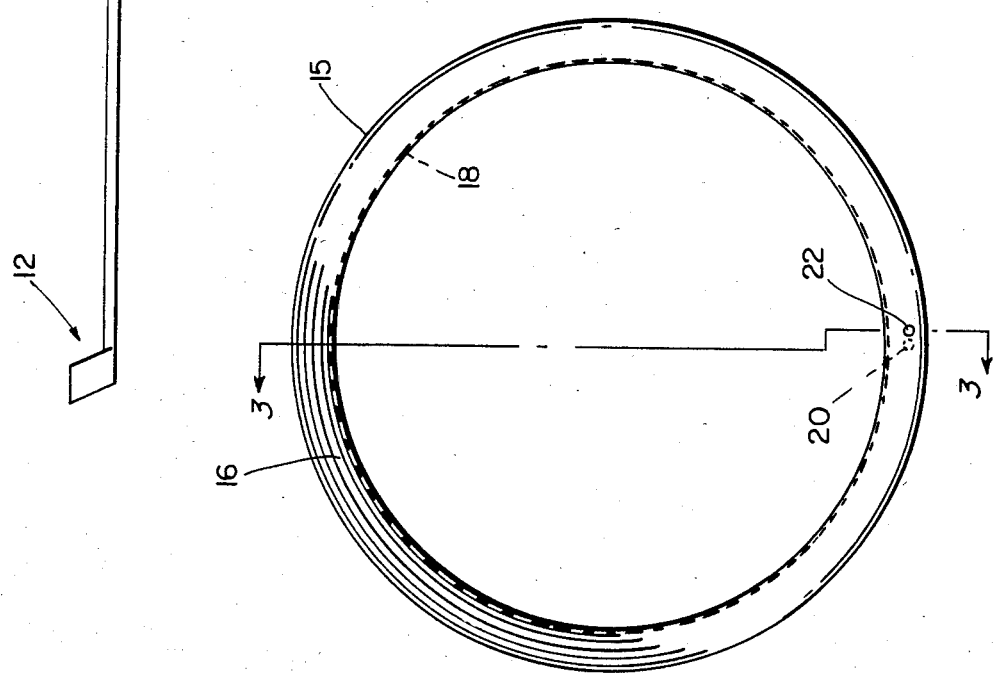

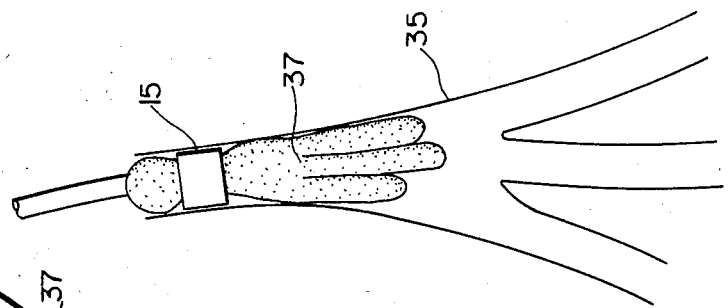
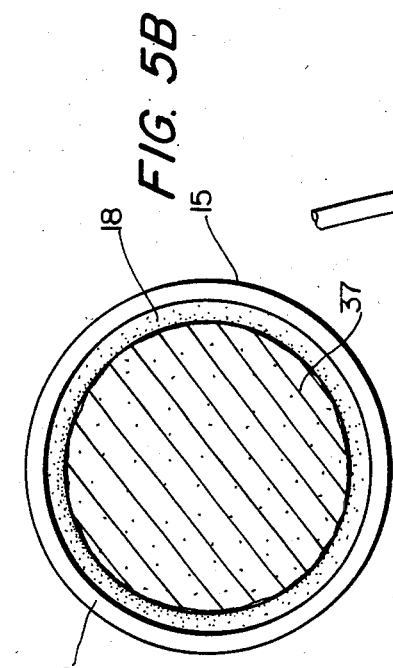
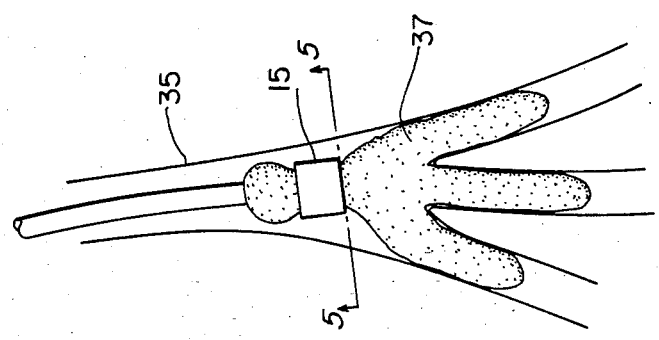
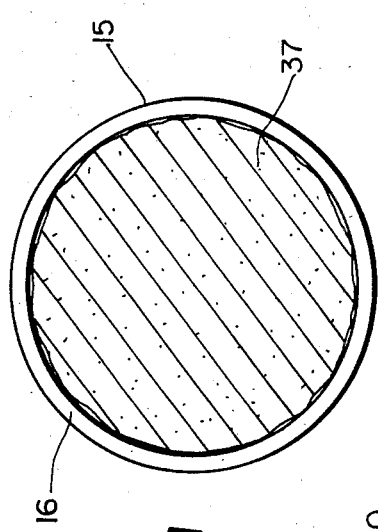
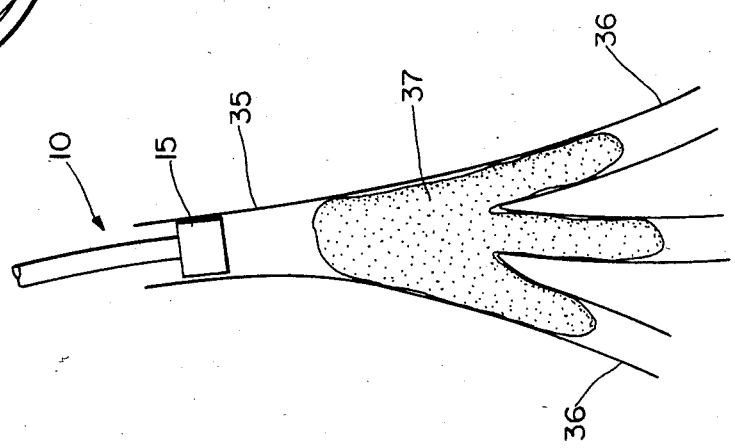

DEVICE FOR REMOVING OBJECTS FROM TUBULAR BODY PASSAGES

This application is a continuation, of application Ser. No. 430,016 filed Sept. 30, 1982 Device and Method for Removing Objects from Tubular Body Passages, now abandoned.

BACKGROUND OF THE INVENTION

This invention relates to the removal of objects from tubular body passages, and it relates in particular to a new and improved method and device for removing such objects.

There are numerous medical situations in which an object becomes positioned in a tubular body passage under conditions which can cause damage to the person. The most significant of these conditions involves the formation of blood clots in the arterial passages. Other conditions involving such blockages include stones located in the urinary passages and foreign objects blocking the esophagus. Although the present invention is applicable for removing any of these or other non-liquid objects located within a tubular body passage, the more significant situation relates to blood clots. Accordingly, while the present invention is adaptable for removing objects in any of the body's tubular passages, it will be described in particular with reference to removal of blood clots in the arterial passageways.

Heretofore it is believed that two approaches have been developed for the removal of blood clots (for example, emboli, thrombi, etc.) from arterial or venous systems. One of these concepts, which has been used successfully only for extracting pulmory emboli involves the use of a catheter having a suction cup at the end thereof.

Another approach which has more universal application is a catheter having a balloon at the distal end thereof which inflates outwardly to use the mechanism of fluid displacement for removing the clots. Such an arrangement is known as the Fogarty Arterial Embolectomy Catheter, hereinafter referred to as the balloon catheter. Such an arrangement is shown generally in the Fogarty U.S. Pat. No. 4,338,942. However, considerable disadvantages have been found to exist with respect to the balloon catheter. One problem is that the catheter is forced directly through the clot which pushes a portion thereof further distally in the arterial tree. On occasion, these portions are unretrievable. A second problem is that when the balloon is inflated and expands outwardly, a portion of the clot is forced outwardly to press against the interior wall of the artery. When the balloon is withdrawn, the portion which was pressed against the interior wall creates a "snow plow" effect which means in effect that a small portion of the clot is deposited at the smaller branches of the artery which it passes, blocking them off. A third problem associated with the prior balloon catheter, which is perhaps the most serious problem, is that if the balloon should be over inflated, it can cause severe and irreparable damage to the interior wall of the artery. In fact, if the balloon is over inflated to the point of rupturing the artery (which does in fact occur) not only is the interior wall damaged, but a portion of the balloon remains inside of the artery, blocking blood flow and quite possibly leading to the loss of a limb.

Hence, there exists a need for improvements in the field of removing objects from tubular body passages, especially arterial passageways, wherein the disadvantages of the prior art are overcome.

SUMMARY OF THE INVENTION

Hence, it is a purpose of the present invention to provide a new and improved method and device for removing objects from tubular body passages, and in particular arterial passageways, wherein the disadvantages of the prior art are overcome.

This purpose is achieved in accordance with the present invention by providing a method and device whereby a ring of relatively stiff material is moved through the tubular body passage until the distal end thereof reaches and surrounds the object to be removed, at which time a balloon located on the interior of this ring is inflated to move only inwardly, being restrained by the ring against outward movement. The inwardly moving balloon grasps the object, after which reverse movement of the ring carries the object back through the tubular passage and out of the body. In a preferred arrangement of the present invention, the device comprises a hollow, pliable body having the ring with the inflatable balloon located therein at the distal end. A pair of fluid lines preferably extend from the distal end through the pliable body to the proximal end. At the distal end, one of these lines is connected to the interior of the balloon to inflate and deflate the same while the other extends to an exit opening at the distal end of the ring for delivering a dye liquid forwardly of the ring, in a manner and for a purpose to be described below. At the proximal end, the device preferably includes a pair of syringes, one for each of the fluid lines. In order to adapt the device for different tubular body passages of different sizes and for insertions of the ring for different distances along the body passages, the devices of the present invention may be provided in a plurality of different sizes including different lengths and different caliber rings.

Hence, it is an object of the present invention to provide a new and improved device for removing objects from tubular body passages.

It is still another object of the present invention to provide a new and improved device for removing blood clots from arterial passageways.

It is still another object of the invention to provide a new and improved method for removing objects such as blood clots from tubular body passages such as arterial passages.

It is still another object of the present invention to provide a new and improved device and method whereby inward movement of an inflatable balloon is used for engaging and grasping an object in a tubular body passage to remove the object.

It is still another object of the present invention to provide a new and improved device having an elongated element with a ring located at the distal end thereof, the ring having an inflatable balloon on the inside thereof which inflates only inwardly, wherein such inward inflation is utilized to grasp an object for removal of that object from the tubular body passage.

These and other objects of the present invention will become apparent from the detailed description to follow, taken together with the accompanying drawings.

BRIEF DESCRIPTION OF THE DRAWINGS

There follows a detailed description of preferred embodiments of the invention to be read together with the accompanying drawings wherein:

FIG. 1 is a side elevational view of the device of the present invention.

FIG. 2 is an end view of FIG. 1, taken from the left hand end, i.e., the distal end, and drawn on an enlarged scale.

FIG. 3 is a cross-sectional view taken along line 3—3 of FIG. 2.

FIG. 4 illustrates a first stage in the operation of the present invention for removing a blood clot from an artery.

FIG. 5a is a cross-sectional view taken through the plane of line 5—5 of FIG. 6, shown at the stage when the ring surrounds the blood clot but wherein the inner balloon has not yet been inflated.

FIG. 5b is also a view taken along line 5—5 of FIG. 6, but after the balloon has been inflated.

FIG. 6 is another view showing the operation of the present invention after the stages shown in FIGS. 4 and 5a and concurrently with the stage shown in FIG. 5b.

FIG. 7 illustrates a further stage in the operation of the present invention.

DETAILED DESCRIPTION OF THE PREFERRED EMBODIMENTS

Referring now to the drawings, like elements are represented by like numerals throughout the several views.

Referring to FIG. 1, there is shown the removal device 10. The central portion thereof comprises a pliable hollow tube 11 having a 360° closed distal end 12 and an open proximal end 13.

The distal end 12 is best shown in FIGS. 2 and 3. As shown therein, the distal end is formed essentially as a ring 15 having a front or distal end which is beveled, as shown at 16 and an open rear or proximal end opposite the distal end. The forward most lip of this bevel is somewhat rounded so as to facilitate movement of the ring through a tubular body passage. The exterior of ring 15 is essentially cylindrical. The interior of ring 15 is also essentially cylindrical except for the formation of an annular recess 17 which receives therein annular inflatable balloon 18. This balloon is shown in FIGS. 2 and 3 in its deflated stage in which the inward facing portion thereof is generally flush and aligned with the interior wall of the ring 15. As is evident from FIGS. 2 and 3, the elongated opening through the ring from its distal opening to its proximal opening is substantially unobstructed when the balloon is deflated. Also shown in FIGS. 2 and 3 are a pair of fluid lines including a dye line 19 and an air line 20. These are shown passing through a central passageway 21 formed in the bottom of the ring 15. This passageway continues rearwardly into the hollow interior of pliable tube 11 through which these lines continue back to the proximal end of the device, as described below.

The dye line 19 continues forwardly beneath the bottom outer surface of the balloon 18 to a discharge outlet 22 located at the forward, distal end of ring 15. The air line 20 terminates at its communication with the interior of recess 18. Its purpose is to provide air or any other fluid for inflating the balloon 18.

At the rear or proximal end, the device includes an adapter 27 having connected thereto a pair of syringes 28 and 29 for delivering dye fluid to dye line 19 and air to the air line 20, respectively.

The removal device of the present invention has been developed with specific features for safe, effective extraction of objects in a tubular body passage such as an emboli in an arterial passageway. The hollow body 11 and the ring 15 may be provided in different lengths and different diameters for use in different tubular body passageways, and in particular for use in different blood vessels. The tube 11 is long enough to permit the ring 15 to be inserted into the tubular passageway such as an acutely occluded vessel as far as possible.

When the balloon is in its inflated state and grasping an object located therein, because of the mechanism of fluid displacement the balloon maintains uniform, even contact with the vessel wall as the ring is withdrawn through narrow areas. Because of this, it is possible to remove thrombotic matter distal to the point of entry. The person operating the device such as a surgeon would hold the device with one hand and manipulate the air syringe 29 with the other. This enables him to judge the amount of traction required for extraction of the object, i.e., the occluded material, as well as the quantity of fluid necessary to effect alternate inflation and deflation as the device is withdrawn through areas of narrowing or increasing vessel diameter.

As noted above, the ring may be made of different sizes. Preferably, these will range from 2 mm to 7 mm in order to fit vessels of different sizes.

The operation of the device and the method of the present invention will now be described, especially with reference to FIGS. 4–7. Although the invention can be used for removing objects from any tubular body passage, for purposes of illustration the operation of the present invention will be described with respect to removal of a blood clot from an arterial passageway.

Having formed an opening through the skin into an arterial passageway at a convenient location relative to the clot, the ring 15 at the distal end of the device is inserted through the opening and into the passageway and moved carefully therealong towards the clot. The rounded forward outer edge of ring 15 facilitates movement of the ring through the passage. Also, as noted in FIG. 3, the forward distal end of the ring lies in a plane which is inclined relative to the axis of ring 15. This also facilitates movement of the ring along the passageway. FIG. 4 illustrates the ring 15 moving along artery 35 toward a blood clot 37 which is located at the juncture of artery 35 and smaller artery branches 36. The ring 15 continues to move forwardly onto the clot, causing a portion thereof to slip inside of the ring 15 and move through the substantially unobstructed opening formed by the ring 15 between its distal opening and its proximal opening. At this time syringe 29 is operated to inflate the balloon 18, causing it to move inwardly to grasp the clot 37. Compare FIGS. 5a and 5b which show a cross section of the ring before and after the balloon has been inflated. FIG. 6 illustrates the ring 15 located on the clot with the inflated balloon grasping the same. The device is now withdrawn by reverse movement of the entire device, pulling the ring 15 rearwardly, bringing the clot with it, as shown in FIG. 7. Since the balloon encircles the clot rather than forces it outward, the snow plow effect which results from outwardly expanding balloons is eliminated. Also, since the balloon cannot move outwardly, the balloon cannot be over inflated and hence cannot rupture or cause any damage to the interior wall of the artery. Also, since the ring goes around the clot and does not push through it, the device will not push portions of the clot further in the distal direction.

Although the invention has been described in considerable detail with respect to preferred embodiments thereof, it will be apparent that the invention is capable of numerous modifications and variations, apparent to those skilled in the art, without departing from the spirit and scope of the invention, as defined in the claims.

We claim:

1. A device comprising means for removing objects from a tubular body passage comprising:
an elongated element having means for being movable through the interior of a tubular body passage without cutting into the interior walls thereof to a place a distal end thereof at a predetermined location within the body passage at which it surrounds an object which is located in the body passage and which is to be removed,
said means for being movable including at said distal end of the device a rigid ring which forms a full 360° closed circle and is of a small enough size to be movable through the interior of a body passage and which constitutes a means for surrounding the object, an inflatable balloon positioned inside of said ring means, said inflatable balloon comprising a means being movable radially inwardly, relative to the ring, upon inflation thereof, the ring itself for its full 360° constituting a means for prohibiting outward movement of the inflatable balloon upon inflation thereof, said ring having an opening at its distal end and an opening at its proximal end, said openings being large, relative to the thickness of the ring, such that the ring forms a large elongated opening therethrough from its distal to its proximal end, which elongated opening is substantially unobstructed when the balloon is uninflated, so that as the ring moves through the body passage with the balloon uninflated, the ring surrounds objects in the body passage which are in turn movable through the said openings of the ring,
means for selectively introducing fluid into the inflatable balloon to cause said inward inflation thereof,
the said ring, when surrounding the object with a balloon inflated inwardly engaging and grasping the object constituting a means for grasping the object and removing the object upon withdrawal of the ring from the tubular body passage,
said ring means having a cylindrical exterior and an inwardly beveled distal end shaped to facilitate movement of the ring through the tubular body portion and around the object, and the distal end of the ring means lying in a plane which is inclinded relative to the axis of the ring, such that only one portion of the ring means leads the rest as the ring means is moved through the tubular body passage.

2. A device according to claim 1, said ring means further having a generally cylindrical interior wall with an annular recess formed into the interior wall, the inflatable balloon being annular and being located in the recess with its radially inward facing surface generally coextensive with said interior wall when the balloon is in its deflated condition.

3. A device comprising means for removing objects from a tubular body passage comprising,
an elongated element having means for being movable through the interior of a tubular body passage without cutting into the interior walls thereof to place a distal end thereof at a predetermined location within the body passage at which it surrounds an object which is located in the body passage and which is to be removed,
said means for being movable including at said distal end of the device a rigid ring which forms a full 360° closed circle and is of a small enough size to be movable through the interior of a body passage and which constitutes a means for surrounding the object, an inflatable balloon positioned inside of said ring means, said inflatable balloon comprising a means being movable radially inwardly, relative to the ring, upon inflation thereof, the ring itself for its full 360° constituting a means for prohibiting outward movement of the inflatable balloon upon inflation thereof, said ring having an opening at its distal end and an opening at its proximal end, said openings being large, relative to the thickness of the ring, such that the ring forms a large elongated opening therethrough from its distal to its proximal end, which elongated opening is substantially unobstructed when the balloon is uninflated, so that as the ring moves through the body passage with the balloon uninflated, the ring surrounds objects in the body passage which are in turn movable through the said openings of the ring,
means for selectively introducing fluid into the inflatable balloon to cause said inward inflation thereof,
the said ring, when surrounding the object with a balloon, inflated inwardly engaging and grasping the object constituting a means for grasping the object and removing the object upon withdrawal of the ring from the tubular body passage,
and including a fluid line leading from the balloon, along the elongated element to the proximal end of the device, and means at the proximal end of the device for introducing fluid into and removing fluid from the line and hence into and from the balloon, and further including a dye line leading from the distal end of the device, along the elongated element to the proximal end of the device, and means at the proximal end of the device for instroducing dye into the dye line.

4. A device according to claim 3, including an adapter at the proximal end of the device, a pair of syringes connected to the adapter, one of said syringes being connected to the fluid line for introducing fluid into the balloon, and the other syringe being connected to the dye line for introducing dye into the dye line.

* * * * *